United States Patent [19]

Mrusek et al.

[11] Patent Number: 5,409,686
[45] Date of Patent: Apr. 25, 1995

[54] PROCESS FOR PRODUCING YELLOW COPPER (I) OXIDE WITH NARROW PARTICLE SIZE RANGE

[75] Inventors: Gerd Mrusek, Buxtehude; Hermann Winkler, Recklingshausen; Michael Stelter; Klaus P. Hugk, both of Hamburg, all of Germany

[73] Assignee: Norddeutsche Affinerie Aktiengesellschaft, Hamburg, Germany

[21] Appl. No.: 814,182

[22] Filed: Dec. 19, 1991

Related U.S. Application Data

[63] Continuation of Ser. No. 396,566, Aug. 21, 1989, abandoned.

[30] Foreign Application Priority Data

Aug. 26, 1988 [DE] Germany .................... 38 28 935.0

[51] Int. Cl.⁶ ............................................. C01G 3/02
[52] U.S. Cl. ............................. 423/604; 423/35; 423/42
[58] Field of Search .............. 423/604, 35, 42; 204/96, 106; 424/635

[56] References Cited

U.S. PATENT DOCUMENTS

| 1,963,105 | 6/1934 | Swift | 423/604 |
|---|---|---|---|
| 2,273,708 | 2/1942 | Hurd | 423/604 |
| 2,474,533 | 6/1949 | Klein | 423/604 |
| 2,507,008 | 5/1950 | Harshaw et al. | 423/604 |
| 2,586,579 | 2/1952 | Supiro | 423/34 |
| 2,923,655 | 2/1960 | Vesterman | 424/635 |

FOREIGN PATENT DOCUMENTS

| 924051 | 7/1947 | France | 423/604 |
|---|---|---|---|
| 929960 | 1/1948 | France . | |
| 384965 | 11/1923 | Germany . | |
| 1042557 | 3/1954 | Germany | 423/604 |
| 1020010 | 2/1958 | Germany . | |
| 184336 | 6/1963 | Sweden | 423/604 |
| 147958 | 7/1920 | United Kingdom | 423/604 |
| 440755 | 2/1927 | United Kingdom . | |
| 309966 | 4/1929 | United Kingdom | 423/604 |
| 489222 | 7/1938 | United Kingdom . | |
| 760079 | 10/1956 | United Kingdom | 424/635 |
| 772846 | 4/1957 | United Kingdom . | |

OTHER PUBLICATIONS

Allison Butts, *Copper*, The Science and Technology of the Metal, Its Alloys and Compounds, 1954, pp. 790–791, 802, 818–819 (no month).

A. F. Holleman; E. Wiberg; Lehrbuch Der Anorganischen Chemie; Walter De Gruyter & Co.; Berlin 1964; pp. 465–466 (no month).

*Primary Examiner*—Steven Bos
*Attorney, Agent, or Firm*—Herbert Dubno; Jonathan Myers

[57] ABSTRACT

In a process of producing copper(I) oxide by the action of an aqueous solution of a mineral acid and of oxygen-containing gas on small-lump copper metal with continuous agitation, a temperature from 10° to 40° C., preferably from 15° to 35° C., is maintained to effect a formation of particulate yellow copper(I) oxide ($Cu_2O$). An organic acid of the group consisting of formic acid, acetic acid, ascorbic acid, preferably ascorbic acid, may be used in addition to the mineral acid.

5 Claims, No Drawings

PROCESS FOR PRODUCING YELLOW COPPER (I) OXIDE WITH NARROW PARTICLE SIZE RANGE

This is a continuation of application Ser. No. 07/396,566 filed on Aug. 21, 1989, now abandoned.

FIELD OF THE INVENTION

My present invention relates to a process for producing finely divided particulate yellow copper(I) oxide, especially for use as the active ingredient in plant-protective pesticides.

BACKGROUND OF THE INVENTION

U.S. Pat. No. 1,963,105 discloses the production of copper(I) oxide in a process in which copper metal suspended in water is subjected to the action of an oxygen-containing gas with agitation and at temperatures between 50° and 100° C. The reaction is promoted by an addition of alkali or alkaline earth metal halides. The product is used as paint for ships.

British Patent Specification 772,846 discloses the production of copper(I) oxide in a process in which an oxygen-containing gas acts on small-lump copper metal, which is suspended in an aqueous mineral acid, at temperatures not below 90° C. and with agitation and while a gauge pressure of 0 to 6 atmospheres is maintained.

The known processes virtually always result in the formation of red copper(I) oxide although changes in color and in particle size from 1 to 3 micrometers can be effected by an addition of adjuvants and a change of the pressure and temperature.

OBJECTS OF THE INVENTION

It is an object of the invention to provide a highly particulate copper(I) oxide which has a bright yellow color and can be used as a pesticide.

Another object of the invention is to provide a process for producing reproducibly $Cu_2O$ in a yellow finely divided form with an extremely small particle size and a small particle size range and which is highly suspendable in water.

DESCRIPTION OF THE INVENTION

These objects are achieved by a process of producing copper(I) oxide by the action of an aqueous solution of a mineral acid and of oxygen-containing gas on small-lump copper metal with continuous agitation.

In accordance with my invention, the process is carried out at a temperature from 10° to 40° C., preferably from 15° to 35° C., to effect a formation of particulate yellow copper(I) oxide ($Cu_2O$).

More specifically, the invention comprises the steps of:

(a) continuously agitating small lumps of copper metal in an aqueous solution of a mineral acid forming a reaction medium and in the presence of an oxygen-containing gas;

(b) controlling the temperature of the reaction medium to maintain it at a temperature of 10° to 40° C. to effect a formation of particulate yellow $Cu_2O$; and (c) recovering the particulate yellow $Cu_2O$ from the reaction medium.

An extremely fine copper(I) oxide having a particle size from 0.05 to 0.4 micrometers is produced by the process in accordance with the invention. The product has a bright yellow color and has a high suspendability of at least 98% (suspendability in accordance with CIPAC Handbook, MT 15.1).

The process in accordance with the invention may be carried out as a pressureless leaching process with agitation. In that process, water is charged into a coolable agitating reactor, which is provided with a bottom scraper and an aerating agitator.

While an agitation is effected, lump metal copper in the form of wire sections or nuggets (bulk density 2 to 6 kg/1 Cu), up to 5 mm in diameter is charged into the agitating container in an amount of 200 to 500 g/l suspension and about 0.50 g mineral acid is added per liter of the suspension. The order in which said actions are performed is not essential.

Agitation is effected suitably with an effectively suspending agitator or an aerating agitator imparting to the suspension a peripheral velocity from 5 to 15 m/sec. An oxygen-containing gas or oxygen is blown into the suspension. A temperature in a range from 15° to 30° C. is preferably maintained.

Hydrochloric acid or hydrobromic acid is suitably used as a mineral acid. In addition to the hydrohalic acids, sulfuric acid may be used. But in order to preclude a coprecipitation of basic copper sulfate, the co-use of an organic acid from the group consisting of ascorbic acid, formic acid and acetic acid is desirable. A co-use of ascorbic acid is preferred.

By the process in accordance with the invention, a yellow copper(I) oxide having a very small particle size can be produced if the suspension is agitated at a higher velocity or if colloids are added. The leaching rate is usually about 5 to 10 g/l per hour.

The process in accordance with the invention can be performed as a batch process or as a continuous process.

If the process in accordance with the invention is carried out as a batch process, care must be taken that the yellow copper(I) oxide is filtered off as soon as the leaching has been terminated because a prolonged standing of the $Cu_2O$ suspension will result in an increase of the particle size range by 0.5 to 1 micrometer and in a color change or in an increase of the saturation of the color of the $Cu_2O$.

Due to its small particle size and its high susceptibility, the yellow copper(I) oxide produced in accordance with the invention constitutes an eminently suitable active ingredient of pesticides. Such compounds which contain yellow copper (I) oxide may be composed, e.g. of about 56% by weight $Cu_2O$, 42% by weight chalk and 2% by weight cell pitch.

For this reason, the invention relates also to the use of yellow copper(I) oxide having a particle size from 0.05 to 0.4 micrometer and a susceptibility of at least 98 (in accordance with CIPAC) as an active ingredient in pesticides.

Advantages are afforded by the invention. By the process in accordance with the invention, yellow copper(I) oxide having a particle size below 0.5 micrometer can be produced in a simple and economical procedure by leaching with agitation and at room temperature from copper metal lumps or pieces of copper wire. Due to its small particle size, the yellow copper(I) oxide produced in accordance with the invention has a high susceptibility in excess of 98. The yellow copper(I) oxide may be used to special advantage as an active ingredient in agricultural pesticides.

SPECIFIC EXAMPLES

The invention will be explained in greater detail with reference to the following Examples.

EXAMPLE 1

10 m$^3$ of water were charged into an open agitating reactor, which had a capacity of 15 m$^3$ and was equipped with a bottom scraper, cooling means and an aerating agitator.

2770 kg of copper wire pieces having a bulk density of 4 kg/l and 2 to 5 mm in diameter and having a length of 2 to 10 mm were suspended in the water with agitation.

Hydrochloric acid and sulfuric acid were subsequently added to the suspension so that the latter contained 0.25 g/l HCl and 0.5 g/l H$_2$SO$_4$. During an intense agitation (72 r.p.m.) oxygen (2 to 5 liters O$_2$/h per liter of suspension) was introduced into the suspension. A temperature of 30° C. was maintained during the leaching.

The leaching reaction was terminated after 6 hours. The dissolving rate amounted to 7.1 g Cu$_2$O/liter per hour.

The suspension of copper(I) oxide was aspirated off through an immersed tube, which was closed at its bottom end by a fine-mesh screen, and the suspension was then filtered on a chamber filter press. The reaction product consisted of a yellow copper(I) oxide product which contained more than 95% Cu$_2$O having a particle size of 0.1 to 0.3 micrometer and a susceptibility of 99 (in accordance with the CIPAC Handbook, Cambridge, U.K., 1970, MT 15.1).

EXAMPLE 2

10 m$^3$ of water were charged into an open agitating vessel (15 m$^3$, equipped with a bottom scraper, a cooler and an aerator).

2800 kg copper wire sections like those used in Example 1 were suspended in the water. 16.3 liters 30% hydrochloric acid and 55 kg ascorbic acid were added.

During a vigorous agitation (about 80 r.p.m.), the suspension was aerated with oxygen (3.4 liters O$_2$/h per liter of suspension). Leaching was effected at 30° C. After 6 hours, the leaching rate amounted to 5.1 g Cu$_2$O/liter per hour. A very fine yellow copper(I) oxide having a particle size range from 0.05 to 0.1 micrometer was obtained. The separation of the copper(I) oxide from the remaining suspension was effected as in Example 1. The product had a susceptibility in excess of 99% (in accordance with CIPAC).

I claim:

1. A process for producing yellow copper(I)oxide having a particle size range of 0.05 to 0.4 micrometers in an open reactor, comprising the steps of:
    (a) in a reactor open to the atmosphere continuously agitating small lumps of copper metal in an aqueous solution of a mineral acid and forming a suspension of said lumps and said solution in said reactor so that said reactor contains 200 to 500 g of said lumps of copper metal per liter of said suspension;
    (b) blowing a gas containing O$_2$ gas into said suspension containing 200 to 500 g of said lumps of copper metal per liter of said suspension;
    (c) cooling said reactor open to the atmosphere to maintain the suspension at a temperature of 10° to 35° C. to effect a formation of particulate yellow copper (I) oxide therein; and
    (d) recovering from said suspension said yellow copper (I) oxide having a particle size range of 0.05 to 0.4 micrometers.

2. The process defined in claim 1 wherein the small lumps of copper metal are in the form of wire pieces or nuggets having a bulk density of 2 to 6 kg/l and said suspension has imparted thereto during a reaction in step (b) and agitation in step (a) a peripheral velocity of 5 to 15 m/sec, said temperature being 15° to 30° C.

3. The process defined in claim 1 wherein said mineral acid is selected from the group consisting of hydrochloric acid and hydrobromic acid.

4. The process defined in claim 1 wherein at least one organic acid is incorporated in said suspension and is selected from the group consisting of formic acid, acetic acid and ascorbic acid.

5. The process defined in claim 4 wherein said organic acid is ascorbic acid.

* * * * *